United States Patent [19]

Bergh

[11] Patent Number: Plant 5,298

[45] Date of Patent: Oct. 23, 1984

[54] AVOCADO TREE—'GWEN'

[75] Inventor: Berthold O. Bergh, Riverside, Calif.

[73] Assignee: The Regents of the University of California, Berkeley, Calif.

[21] Appl. No.: 467,613

[22] Filed: Feb. 17, 1983

[51] Int. Cl.[3] ..... A01H 5/03

[52] U.S. Cl. ..... Plt./44

[58] Field of Search ..... Plt./44

*Primary Examiner*—Robert E. Bagwill

*Attorney, Agent, or Firm*—Townsend and Townsend

[57] ABSTRACT

A new and distinct variety of avocado tree characterized by its small tree size and high productivity (about twice that of 'Hass'). The variety is also characterized by the virtual absence of russeting of its fruit and by the richness of its fruit flavor.

2 Drawing Figures

DESCRIPTION

This invention relates to a new and distinct variety of avocado tree designated as 'Gwen' and tested as selection T225.

'Gwen' is a "grandchild" of 'Hass' and has been propagated asexually by T-budding, whip-grafting, saddle-grafting and saw-kerf grafting at the University of California, Riverside and South Coast Field Station facilities in Southern California where the variety has been tested.

Figure 1:
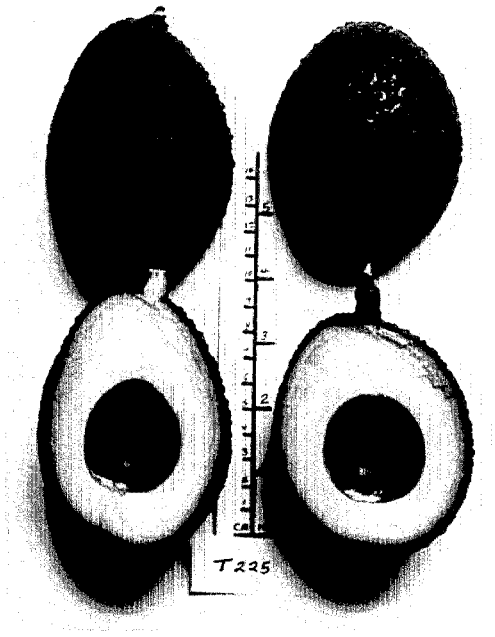
FIG. 1 shows typical fruiting characteristics of the tree.
Figure 2:
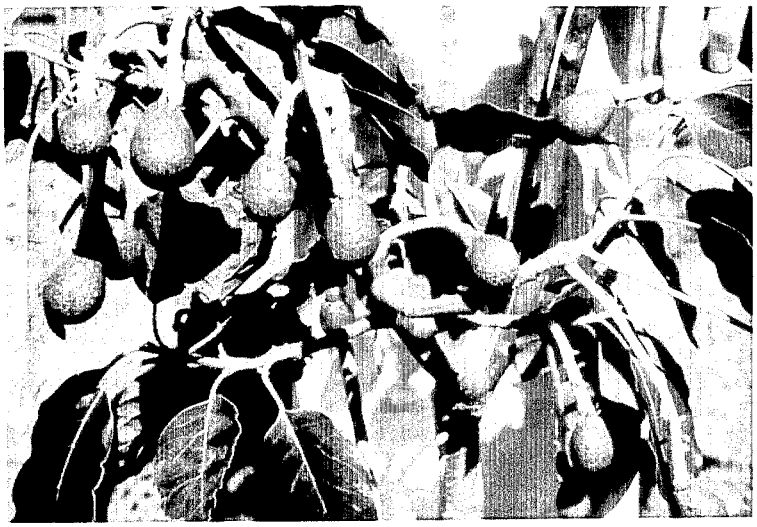
FIG. 2 shows the heavy fruit-set ability typical of the tree.

'Gwen' has two primary characteristics which distinguish it. It is a much smaller tree than 'Hass' resulting in smaller picking costs and its production per acre is about twice as great as 'Hass' based upon the performance of several trees tested over several years in both test areas.

No resistance of 'Gwen' is known to the few insects which are rarely a problem to avocado trees, nor to Verticillium wilt, the Black-streak disease or the Sunblotch viroid. Resistance to Phytophthora is a property of the rootstock and not the scion top. In resistance to the physiological disease of freezing injury, 'Gwen' rates "tender" and is about comparable to the 'Hass' standard.

It is impossible to assign very meaningful distinctions of the new variety based upon color. With reference to the Horticultural Colour Charts (issued by Wilson Colour Ltd. in collaboration with The Royal Horticultural Society) typically 'Gwen' has the background skin color Spinach Green o960 (Repertoire, Vert Epinard 270/4). The basic green skin color not only varies of itself but is flecked with numerous tiny islands of varying yellowish shades. Moreover, the two halves of the fruit usually differ in average color. Each average color differs according to the time of fruit-set (which may vary widely on a tree), the degree of maturity, geographic location, and possibly other factors. Nevertheless, the above-identified is the most consistent color skin of the fruit of this variety.

TREES AND FOLIAGE

'Gwen', as in the case of most avocado cultivars, does not have distinctive foliage and cannot consistently be distinguished from 'Hass' on the basis of leaf, flower, or limb traits. In tree form 'Gwen' is moderately upright, short, small and slim. Leaves are rather like 'Hass' and the tree has moderate vigor.

FRUIT

Ovate; about 250 grams (similar to 'Hass') fine-speckled roughness; almost no russeting, even past maturity. Flesh about like 'Hass'; flavor even richer than 'Hass'; seed averages larger than 'Hass'. Production is consistently heavy with exceptionally little alternation. The season is about March through September.

I claim:

1. The new and distinct varity of avocado tree herein described and illustrated and identified by the characteristics enumerated above.

* * * * *